(12) United States Patent
Dufay et al.

(10) Patent No.: US 7,279,456 B2
(45) Date of Patent: Oct. 9, 2007

(54) SURFACTANT MIXTURES

(75) Inventors: Daniel Dufay, Courtenay (FR); Beatrice Hallé, Perthes (FR)

(73) Assignee: Gognis France S.A., Saint-Martory (FR)

( * ) Notice: Subject to any disclaimer, the term of this patent is extended or adjusted under 35 U.S.C. 154(b) by 157 days.

(21) Appl. No.: 10/480,558

(22) PCT Filed: Jun. 6, 2002

(86) PCT No.: PCT/EP02/06189

§ 371 (c)(1),
(2), (4) Date: Feb. 4, 2005

(87) PCT Pub. No.: WO02/102949

PCT Pub. Date: Dec. 27, 2002

(65) Prior Publication Data

US 2005/0143277 A1    Jun. 30, 2005

(30) Foreign Application Priority Data

Jun. 15, 2001    (FR) .................... 01 07851

(51) Int. Cl.
*C11D 1/94* (2006.01)
*C11D 1/29* (2006.01)
*C11D 1/66* (2006.01)
*C11D 1/90* (2006.01)

(52) U.S. Cl. .................... 510/535; 510/123; 510/127; 510/155; 510/426; 510/433; 510/470; 510/473; 510/474; 510/490; 510/492; 510/504; 424/401; 424/70.13; 424/70.21; 424/70.24

(58) Field of Classification Search ............ 510/123, 510/127, 155, 426, 433, 470, 473, 474, 490, 510/492, 504, 535; 424/401, 70.13, 70.21, 424/70.24
See application file for complete search history.

(56) References Cited

U.S. PATENT DOCUMENTS

| | | | |
|---|---|---|---|
| 4,172,887 A | 10/1979 | Vanlerberghe et al. | |
| 5,374,716 A | 12/1994 | Biermann et al. | |
| 5,576,425 A | 11/1996 | Hill et al. | |
| 5,578,560 A * | 11/1996 | Giesen et al. ............ | 510/237 |
| 5,705,169 A | 1/1998 | Stein et al. | |
| 5,730,960 A | 3/1998 | Stein et al. | |
| 5,945,091 A | 8/1999 | Habeck et al. | |
| 6,015,780 A | 1/2000 | Llosas Bigorra et al. | |
| 6,193,960 B1 | 2/2001 | Metzger et al. | |
| 6,210,659 B1 | 4/2001 | Wilhelm et al. | |

FOREIGN PATENT DOCUMENTS

| | | |
|---|---|---|
| DE | 11 65 574 | 8/1960 |
| DE | 20 24 051 | 12/1970 |
| DE | 197 56 377 | 12/1997 |
| DE | 197 12 033 | 9/1998 |
| DE | 197 23 763 | 12/1998 |
| DE | 199 17 745 | 3/2000 |
| DE | 19917745 | * 3/2000 |
| EP | 0 301 298 | 2/1989 |
| EP | 0 341 071 | 11/1989 |
| EP | 0 670 158 | 6/1995 |
| EP | 0 664 830 | 8/1995 |
| EP | 0 693 471 | 1/1996 |
| EP | 0 694 521 | 1/1996 |
| EP | 0 763 591 | 3/1997 |
| EP | 0 818 450 | 1/1998 |
| FR | 2 252 840 | 6/1975 |
| GB | 962919 | 7/1964 |
| GB | 1333475 | 10/1973 |
| WO | WO90/03977 | 4/1990 |
| WO | WO91 115 06 | 8/1991 |
| WO | WO94 09102 | 4/1994 |
| WO | WO96/29385 | 9/1996 |
| WO | WO96 41858 | 12/1996 |
| WO | WO97/38072 | 10/1997 |
| WO | WO98 20844 | 5/1998 |
| WO | WO98 26036 | 6/1998 |
| WO | WO98/36043 | 8/1998 |
| WO | WO98/46721 | 10/1998 |
| WO | WO99 27062 | 6/1999 |

OTHER PUBLICATIONS

J. Falbe, "Surfactants in Consumer Products", Springer Verlag, Berlin, 1987, pp. 54-124.
J. Falbe, "Katalysatoren, Tenside und Mineralöladditive", Thieme Verlag, Stuttgart, 1978, pp. 123-217.
R. Lochhead et al., "Encyclopedia of Polymers and Thickeners for Cosmetics", Cosmetics & Toiletries, vol. 108, (May, 1993), pp. 95-135.
C. Todd et al., "Volatile silicone fluids for cosmetic formulations", Cosmetics and Toiletries, vol. 91, (Jan. 1976), pp. 29-32.
P. Finkel, "Formulierung kosmetischer Sonnenschutzmittel", SÖFW-Journal, vol. 122, (1996), pp. 543-546 & 548.
P. Finkel, "Formulierung kosmetischer Sonnenschutzmittel", Parfumerie und Kosmetik, 80, No. 3 (1999), pp. 10-12, 14-16.
Die Kosmetik-Verordnung, Deutsches Institut für Körperpftege und Hygiene e.V., Appendix 6, Parts A and B, no date given.
"Kosmetische Färbemittel", Farbstoffkommission der Deutschen Forschungsgemeinschaft, Verlag Chemie, Weinheim, (1984), pp. 81-106.

* cited by examiner

*Primary Examiner*—Brian Mruk
(74) *Attorney, Agent, or Firm*—John F. Daniels; Daniel S. Ortiz

(57) ABSTRACT

A surfactant composition containing: (a) from about 15 to 20% by weight of an alkyl and/or alkenyl oligoglycoside; (b) from about 15 to 20% by weight of a betaine; and (c) from about 60 to 70% by weight of an alkyl ether sulfate, all weights being based on the weight of the composition.

8 Claims, No Drawings

SURFACTANT MIXTURES

BACKGROUND OF THE INVENTION

This application is a 371 of PCT/EP02/06189 filed Jun. 6, 2002.

This invention relates generally to the cosmetics field and, more particularly, to new ternary mixtures of surfactants and to their use for the production of body care products.

Alkyl oligoglucosides are nonionic surfactants which have acquired particular significance in recent years by virtue of their particular dermatological compatibility. Another advantage of this group of compounds is that, although they do foam to an extent matched only by anionic surfactants, they can be combined far better with other surfactants through the absence of ionic groups.

Accordingly, various surfactant mixtures involving alkyl oligoglucosides are known from the prior art, combinations with a large number of anionic and amphoteric surfactants being preferred from the performance perspective. Thus, ternary combinations of alkyl oligoglucosides, alkyl ether sulfates and betaines, optionally with other cosurfactants, such as fatty alcohol polyglycol ethers, amine oxides, fatty acid amidoamines or alkyl sulfates, have been repeatedly recommended for use in manual dishwashing detergents [EP 0341071 B2 (Unilever), EP 0664830 B1 (Cognis), WO 96/29385, WO 97/38072, WO 98/36043, WO 98/46721 (all Colgate)]. The same mixtures are also used in cleaning products [EP 0670158 A2 (Colgate), WO 91/11506 (Henkel)] and in hair shampoos [DE 19723763 C1 (Goldwell)].

However, this is does not mean that all technical requirements have been satisfied. Mixtures containing anionic surfactants in particular have sometimes been found to show less than optimal dermatological compatibility, especially when used by consumers with sensitive skin. In addition, although highly concentrated flowable mixtures can be produced, such mixtures do form high-viscosity gel phases when diluted so that they are virtually impossible to handle. In addition, most of the known surfactant mixtures can only be protected against microbial infestation by the use of preservatives which is contrary to the concept of a particularly dermatologically compatible surfactant concentrate.

Accordingly, the problem addressed by the present invention was to provide surfactant mixtures which, besides good foaming and cleaning properties, would show improved dermatological compatibility. The mixtures would also be protected against microbial infestation even without the addition of possibly irritating preservatives, so that they could also be used in particular for the production of baby care products. In addition, the preparations would be liquid or flowable even in highly concentrated form and, in particular, would not form any high-viscosity gel phases on dilution.

DESCRIPTION OF THE INVENTION

The present invention relates to new surfactant mixtures consisting based on the solids content—of
(a) 15 to 20% by weight alkyl and/or alkenyl oligoglycosides,
(b) 15 to 20% by weight betaines and
(c) 60 to 70% by weight alkyl ether sulfates, with the proviso that the quantities shown add up to 100% by weight.

It has surprisingly been found that the three components in the quantities shown not only have optimized dermatological compatibility, they are also liquid in highly concentrated form, the formation of an unwanted gel phase—particularly on dilution—being prevented. Finally, preservatives do not have to be added to protect the mixture against microbial infestation.

Alkyl and/or Alkenyl Oligoglycosides

Alkyl and alkenyl oligoglycosides which form component (a) are known nonionic surfactants which correspond to formula (I):

$$R^1O\text{-}[G]_p \quad (I)$$

where $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. EP-A1 0301298 and WO 90/03977 are cited here as representative of the literature abundantly available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational perspective.

The alkyl or alkenyl group $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl group $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Betaines

Examples of suitable betaines which form component (b) are alkyl betaines, alkyl amidobetaines, aminopropionates, aminoglycinates, imidazolinium betaines and sulfobetaines. Alkyl betaines are the carboxyalkylation products of secondary and, in particular, tertiary amines corresponding to formula (II):

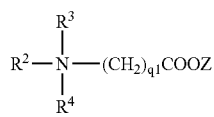

(II)

in which $R^2$ stands for alkyl and/or alkenyl groups containing 6 to 22 carbon atoms, $R^3$ stands for hydrogen or alkyl groups containing 1 to 4 carbon atoms, $R^4$ stands for alkyl groups containing 1 to 4 carbon atoms, q1 is a number of 1 to 6 and Z is an alkali metal and/or alkaline earth metal or ammonium. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof.

Other suitable betaines are carboxyalkylation products of amidoamines corresponding to formula (III):

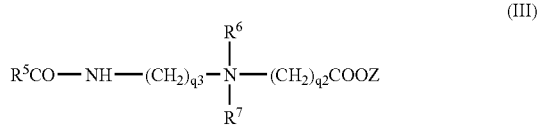

(III)

in which $R^5CO$ is an aliphatic acyl group containing 6 to 22 carbon atoms and 0 or 1 to 3 double bonds, $R^6$ represents hydrogen or $C_{1-4}$ alkyl groups, $R^7$ represents $C_{1-4}$ alkyl groups, q2 is a number of 1 to 6, q3 is a number of 1 to 3 and Z again represents an alkali metal and/or alkaline earth metal or ammonium. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethyl aminoethyl amine, N,N-dimethyl aminopropyl amine, N,N-diethyl aminoethyl amine and N,N-diethyl aminopropyl amine which are condensed with sodium chloroacetate. It is preferred to use a condensation product of $C_{8/18}$ cocofatty acid-N,N-dimethyl aminopropyl amide with sodium chloroacetate.

Imidazolinium betaines are also suitable. These substances are also known substances which may be obtained, for example, by cyclizing condensation of 1 or 2 mol fatty acid with polyfunctional amines, for example aminoethyl ethanolamine (AEEA) or diethylene triamine. The corresponding carboxyalkylation products are mixtures of different open-chain betaines. Typical examples are condensation products of the abovementioned fatty acids with AEEA, preferably imidazolines based on lauric acid or—again —$C_{12/14}$ cocofatty acid which are subsequently betainized with sodium chloroacetate.

Alkyl Ether Sulfates

Alkyl ether sulfates which form component (c) are understood to be the sulfation products of addition products of alkylene oxides onto primary and/or secondary alcohols which preferably correspond to formula (IV):

$$R^8O-(CH_2CHR^9O)_nSO_3X \qquad (IV)$$

in which $R^8$ is a linear or branched, aliphatic alkyl group containing 6 to 22 and preferably 12 to 18 carbon atoms, $R^9$ represents hydrogen or methyl, n is a number of 1 to 30 and X is an alkali metal and/or alkaline earth metal, ammonium, alkylammonium, alkanolammonium or glucammonium. Typical examples of alkyl ether sulfates which may be used in accordance with the invention are the sulfation products of addition products of, on average 1 to 25, preferably 2 to 20 and more particularly 5 to 10 mol ethylene and/or propylene oxide onto caproic alcohol, caprylic alcohol, capric alcohol, 2-ethylhexyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol and erucyl alcohol and the technical mixtures thereof obtained by high-pressure hydrogenation of technical methyl ester fractions or aldehydes from Roelen's oxosynthesis. The sulfation products may advantageously be used in the form of their alkali metal salts, more especially their sodium salts. Alkyl ether sulfates based on $C_{16/18}$ or $C_{12/14}$ coconut fatty alcohols or vegetable fatty alcohols with a comparable C-chain distribution in the form of their sodium salts are particularly preferred. In the case of branched primary types, the alcohols are oxoalcohols which are obtainable, for example, by addition of carbon monoxide and hydrogen onto α-olefins by the Shop process. Corresponding alcohol mixtures are commercially available under the trade names of Dobanol® or Neodol®. Suitable alcohol mixtures are Dobanol 91®, 23®, 25® and 45®. Another possibility are the adducts of alkylene oxides with oxoalcohols obtained by the standard oxo process of Enichema or Condea in which carbon monoxide and hydrogen are added onto olefins. These alcohol mixtures are a mixture of highly branched alcohols and are commercially available under the name of Lial®. Suitable alkyl ether sulfates are, for example, the sulfation products of ethoxylated alcohol mixtures commercially obtainable as Lial 91®, 111®, 123®, 125®, 145®.

The present invention also relates to water-based preparations containing 40 to 80 and preferably 50 to 60% by weight of the ternary surfactant mixtures and water to 100% by weight.

Commercial Applications

The present invention also relates to the use of the ternary surfactant mixtures for the production of cosmetic preparations, especially body care preparations such as, for example, shower gels and shower baths and, in particular, baby care products, in which they may be present in quantities of 1 to 50, preferably 5 to 35 and more particularly 10 to 20% by weight, based on the particular preparation.

Cosmetic and/or Pharmaceutical Preparations

The surfactant mixtures according to the invention may be used for the production of cosmetic preparations such as, for example, hair shampoos, hair lotions, foam baths, shower baths, creams, gels, lotions, alcoholic and hydroalcohollic solutions, emulsions, wax/fat compounds, stick preparations, powders or ointments. These preparations may also contain mild surfactants, oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorizers, antiperspirants, antidandruff agents, film formers, swelling agents, insect repellents, self-tanning agents, tyrosine inhibitors (depigmenting agents), hydrotropes, solubilizers, preservatives, perfume oils, dyes and the like as further auxiliaries and additives.

Surfactants

Suitable surfactants are anionic, nonionic and/or cationic surfactants which may be present in the preparations in quantities of normally about 1 to 70% by weight, preferably 5 to 50% by weight and more preferably 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 197 56 377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, such as Dicaprylyl Carbonate (Cetiol® CC) for example, Guerbet carbonates based on $C_{6-18}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, such as Dicaprylyl Ether (Cetiol® OE) for example, ring opening products of epoxidized fatty acid esters with polyols, silicone oils (cyclomethicone, silicon methicone types, etc.) and/or aliphatic or naphthenic hydrocarbons such as, for example, squalane, squalene or dialkyl cyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide onto linear $C_{8-22}$ fatty alcohols, onto $C_{12-22}$ fatty acids, onto alkyl phenols containing 8 to 15 carbon atoms in the alkyl group and onto alkylamines containing 8 to 22 carbon atoms in the alkyl group;

alkyl and/or alkenyl oligoglycosides containing 8 to 22 carbon atoms in the alk(en)yl group and ethoxylated analogs thereof;

addition products of 1 to 15 mol ethylene oxide onto castor oil and/or hydrogenated castor oil;

addition products of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide;

partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide;

mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethyleneglycol-30 Dipolyhydroxystearate;

polymer emulsifiers, for example Pemulen types (TR-1, TR-2) of Goodrich;

polyalkylene glycols and glycerol carbonate.

Ethylene Oxide Addition Products

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations from DE 2024051 PS.

Alkyl and/or Alkenyl Oligoglycosides

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers

Typical anionic emulsifiers are aliphatic fatty acids containing 12 to 22 carbon atoms such as, for example, palmitic acid, stearic acid or behenic acid and dicarboxylic acids containing 12 to 22 carbon atoms such as, for example, azelaic acid or sebacic acid.

Amphoteric and Cationic Emulsifiers

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, Nhydroxyethyl-N- alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryidimonium Hydroxypropyl Hydrolyzed Collagen (Lamequat® L, Grunau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosm. Toil., 108, 95 (1993).

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor as described in EP 0693471 B1;
- 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomenthyl ester;
- derivatives of benzophenone, preferably 2-hydroxy-4-methoxybenzophenone, 2-hydroxy-4-methoxy4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone as described in EP 0818450 Alor Dioctyl Butamido Triazone (Uvasorb® HEB);
- propane-1,3-diones such as, for example, 1-(4-tert.butylphenyl)-3-(4'-methoxyphenyl)-propane-1,3-dione;
- ketotricyclo(5.2.1.0)decane derivatives as described in EP 0694521 B1.

Suitable water-soluble substances are

- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789) or 1-phenyl-3-(4'-isopropylphenyl)-propane-1,3-dione and the enamine compounds described in DE 19712033 A1 (BASF). The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SÖFW-Journal 122, 543 (1996) and in Parf. Kosm. 3, 11 (1999).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, SuperoxidDismutase, zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prune extract and bambara nut extract, and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-noctyl amide or salicylic acid-n-decyl amide.

Enzyme Inhibitors

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor Absorbers

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, lemon balm oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components, nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Insect Repellents

Suitable insect repellents are N,N-diethyl-m-toluamide, pentane-1,2-diol or Ethyl Butylacetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 dalton;
technical oligoglycerol mixtures with a degree of self-condensation of 1.5 to 10 such as, for example, technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetik-verordnung ("Cosmetics Directive").

Perfume Oils and Aromas

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS(C.I. 69800) and madder lake (C.I. 58000). Luminol may also be present as a luminescent dye. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular preparations. The preparations may be produced by standard hot or cold processes and are preferably produced by the phase inversion temperature method.

EXAMPLES

Ternary mixtures were prepared and adjusted to an active substance concentration of 50% by weight. The concentrates were then adjusted to an in-use concentration of 10% by weight. The viscosities before and after dilution were determined by the Brookfield method (RVT viscosimeter, 20° C., spindle 1, 4 r.p.m.). The results are set out in Table 1. The quantities shown are based on the active substance content of the mixtures.

TABLE 1

Viscosity of surfactant concentrates before and after dilution

| Composition | 1 | 2 | C1 | C2 | C3 |
|---|---|---|---|---|---|
| Coco glucosides | 15.0 | 18.0 | 18.0 | 15.0 | 15.0 |
| Cocamidopropyl Betaine | 15.0 | 12.0 | 18.0 | 30.0 | 10.0 |
| Sodium Laureth Sulfate | 70.0 | 70.0 | 64.0 | 55.0 | 75.0 |
| Viscosity [mPas] | | | | | |
| 50% by weight solution | 5,900 | 6,200 | 6,300 | 6,500 | 6,500 |
| 10% by weight dilution | 1,200 | 1,300 | >10,000 | >10,000 | >10,000 |

It can be seen that it is only within the mixing ratios according to the invention that no gel phase is formed on dilution.

A number of formulation Examples are shown in Table 2.

TABLE 2

Examples for cosmetic preparations (water, preservative to 100% by weight)

| Composition (INCI) | 1 | 2 | 3 | 4 | 5 | 6 | 7 | 8 | 9 | 10 |
|---|---|---|---|---|---|---|---|---|---|---|
| Surfactant mixture of Example 1 Cocoglucosides (and) Cocamidopropyl Betaine (and) Sodium Laureth Sulfate | 38.0 | 38.0 | 45.0 | 45.0 | 45.0 | 25.0 | 25.0 | 25.0 | 19.0 | 19.0 |
| Lanette ® O Cetearyl Alcohol | — | — | — | — | — | — | — | — | — | 1.0 |
| Cutina ® GMS Glyceryl Stearate | — | — | — | — | — | 1.0 | — | — | — | — |
| Cetiol ® HE PEG-7 Glyceryl Cocoate | — | — | — | — | — | — | 1.0 | — | — | — |
| Cetiol ® PGL Hexyldecanol (and) Hexyldecyl Laurate | — | — | — | — | — | — | — | — | 1.0 | — |
| Cetiol ® V Decyl Oleate | — | — | — | — | — | — | — | 1.0 | — | — |
| Eutanol ® G Octyldodecanol | — | — | — | — | — | — | — | — | 1.0 | — |

TABLE 2-continued

Examples for cosmetic preparations (water, preservative to 100% by weight)

| | | | | | | | | | | |
|---|---|---|---|---|---|---|---|---|---|---|
| Nutrilan ® Keratin W<br>Hydrolyzed Keratin | — | — | 1.0 | — | — | — | — | — | — | — |
| Lamesoft ® LMG<br>Glyceryl Laurate (and) Potassium Cocoyl Hydrolyzed Collagen | 3.0 | 2.0 | 5.0 | 2.0 | 8.0 | 4.0 | 4.0 | 4.0 | 3.0 | — |
| Euperlan ® PK 3000 AM<br>Glycol Distearate (and) Laureth-4 (and) Cocamidopropyl Betaine | — | 3.0 | — | 3.0 | — | 5.0 | 5.0 | 5.0 | 5.0 | 5.0 |
| Generol ® 122 N<br>Soja Sterol | — | — | — | 1.0 | — | — | — | — | — | — |
| Hydagen ® CMF<br>Chitosan | 1.0 | 1.0 | 1.0 | 1.0 | 1.0 | 1.0 | 1.0 | 1.0 | 1.0 | 1.0 |
| Copherol ® 1250<br>Tocopherol Acetate | — | — | 1.0 | — | — | — | — | — | — | — |
| Arlypon ® F<br>Laureth-2 | 3.0 | 3.0 | 3.0 | 3.0 | 3.0 | 1.0 | 1.0 | 1.0 | — | — |
| Sodium Chloride | — | 1.5 | — | 1.5 | 1.5 | — | — | — | 1.5 | 1.5 |

| Composition (INCI) | 11 | 12 | 13 | 14 | 15 | 16 | 17 | 18 | 19 | 20 |
|---|---|---|---|---|---|---|---|---|---|---|
| Surfactant mixture of Example 1<br>Cocoglucosides (and) Cocamidopropyl Betaine (and) Sodium Laureth Sulfate | 45.0 | 45.0 | 16.0 | 40.0 | 38.0 | 33.0 | 16.0 | 17.0 | 17.0 | 34.0 |
| Eumulgin ® B1<br>Ceteareth-12 | — | — | — | — | 1.0 | — | — | — | — | — |
| Eumulgin ® B2<br>Ceteareth-20 | — | — | — | 1.0 | — | — | — | — | — | — |
| Lameform ® TGI<br>Polyglyceryl-3 Isostearate | — | — | — | 4.0 | — | — | — | — | — | — |
| Dehymuls ® PGPH<br>Polyglyceryl-2 Dipolyhydroxystearate | — | — | 1.0 | — | — | — | — | — | — | — |
| Monomuls ® 90-L 12<br>Glyceryl Laurate | — | — | — | — | — | — | — | — | 1.0 | 1.0 |
| Cetiol ® HE<br>PEG-7 Glyceryl Cocoate | — | 0.2 | — | — | — | — | — | — | — | — |
| Eutanol ® G<br>Octyldodecanol | — | — | — | 3.0 | — | — | — | — | — | — |
| Nutrilan ® Keratin W<br>Hydrolyzed Keratin | — | — | — | — | — | — | — | — | 2.0 | 2.0 |
| Nutrilan ® I<br>Hydrolyzed Collagen | 1.0 | — | — | — | — | 2.0 | — | 2.0 | — | — |
| Lamesoft ® LMG<br>Glyceryl Laurate (and) Potassium Cocoyl Hydrolyzed Collagen | — | — | — | — | — | — | — | — | 1.0 | — |
| Lamesoft ® 156<br>Hydrogenated Tallow Glyceride (and) Potassium Cocoyl Hydrolyzed Collagen | — | — | — | — | — | — | — | — | — | 5.0 |
| Gluadin ® WK<br>Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM<br>Glycol Distearate (and) Laureth-4 (and) Cocamidopropyl Betaine | 5.0 | 3.0 | 4.0 | — | — | — | — | 3.0 | 3.0 | — |
| Arlypon ® F<br>Laureth-2 | 2.6 | 1.6 | — | 1.0 | 1.5 | — | — | — | — | — |
| Hydagen ® CMF<br>Chitosan | 1.0 | 1.0 | 1.0 | 1.0 | 1.0 | 1.0 | 1.0 | 1.0 | 1.0 | 1.0 |
| Sodium Chloride | — | — | — | — | — | 1.6 | 2.0 | 2.2 | — | 3.0 |
| Glycerol (86% by weight) | — | 5.0 | — | — | — | — | — | 1.0 | 3.0 | — |

(1–5) Shower bath,
(6–8) Shower gel,
(10) Wash lotion
(11–14) "2-in-1" Shower bath,
(15–20) Shampoo

The invention claimed is:

1. A surfactant composition consisting of:
   (a) from about 15 to 20% by weight of an alkyl and/or alkenyl oligoglycoside;
   (b) from about 15 to 20% by weight of a betaine; and
   (c) from about 60 to 70% by weight of an alkyl ether sulfate, all weights being based on the weight of the composition.

2. An aqueous composition comprising from about 40 to 80% by weight of a surfactant mixture consisting of:

(a) from about 15 to 20% by weight of an alkyl and/or alkenyl oligoglycoside;
(b) from about 15 to 20% by weight of a betaine; and
(c) from about 60 to 70% by weight of an alkyl ether sulfate, all weights of surfactants being based on the weight of the sufactant mixture.

3. The composition of claim 2 wherein the composition is free of preservatives.

4. The composition of claim 2 wherein the surfactant mixture is present in the composition in an amount of from about 50 to 60% by weight, based on the weight of the composition.

5. A cosmetic or pharmaceutical composition comprising from about 1 to 50% by weight of a surfactant mixture consisting of:
(a) from about 15 to 20% by weight of an alkyl and/or alkenyl oligoglycoside;
(b) from about 15 to 20% by weight of a betaine; and
(c) from about 60 to 70% by weight of an alkyl ether sulfate, all weights of surfactants being based on the weight of the surfactant mixture.

6. The composition of claim 5 wherein the composition is free of preservatives.

7. The composition of claim 5 wherein the surfactant mixture is present in the composition in an amount of from about 5 to 35% by weight, based on the weight of the composition.

8. The composition of claim 5 wherein the surfactant mixture is present in the composition in an amount of from about 10 to 20% by weight, based on the weight of the composition.

* * * * *